(12) United States Patent
Katra

(10) Patent No.: US 9,901,266 B2
(45) Date of Patent: Feb. 27, 2018

(54) APPARATUS AND METHOD FOR PERSONALIZED CARDIAC SIGNAL PROCESSING

(71) Applicant: Greatbatch Ltd., Clarence, NY (US)

(72) Inventor: Rodolphe Katra, Blaine, MN (US)

(73) Assignee: GREATBATCH LTD., Clarence, NY (US)

( * ) Notice: Subject to any disclaimer, the term of this patent is extended or adjusted under 35 U.S.C. 154(b) by 0 days.

(21) Appl. No.: 14/738,022

(22) Filed: Jun. 12, 2015

(65) Prior Publication Data

US 2016/0256060 A1 Sep. 8, 2016

Related U.S. Application Data

(60) Provisional application No. 62/129,178, filed on Mar. 6, 2015.

(51) Int. Cl.
| | |
|---|---|
| *A61B 5/02* | (2006.01) |
| *A61B 5/024* | (2006.01) |
| *A61B 5/0245* | (2006.01) |
| *A61B 5/00* | (2006.01) |
| *A61B 5/046* | (2006.01) |

(Continued)

(52) U.S. Cl.
CPC ........ *A61B 5/02405* (2013.01); *A61B 5/0245* (2013.01); *A61B 5/046* (2013.01); *A61B 5/4848* (2013.01); *A61B 5/7275* (2013.01); *A61B 5/7282* (2013.01); *A61N 1/3622* (2013.01); *A61N 1/3624* (2013.01); *A61N 1/395* (2013.01); *A61B 5/0022* (2013.01); *A61B 5/0031* (2013.01); *A61B 5/0205* (2013.01); *A61B 5/0488* (2013.01); *A61B 5/053* (2013.01); *A61B 5/1118* (2013.01); *A61B 5/14532* (2013.01);

(Continued)

(58) Field of Classification Search
CPC ................................................. A61B 5/02405
See application file for complete search history.

(56) References Cited

U.S. PATENT DOCUMENTS

| 4,003,974 A | 1/1977 | Chantry et al. |
|---|---|---|
| 6,487,442 B1 | 11/2002 | Wood |

(Continued)

FOREIGN PATENT DOCUMENTS

| CN | 103247010 | 8/2013 |
|---|---|---|
| CN | 103815896 | 5/2014 |

*Primary Examiner* — Eric D. Bertram
(74) *Attorney, Agent, or Firm* — Hollingsworth Davis, LLC

(57) ABSTRACT

A medical device includes a housing configured for implantation within a body of a patient. Detection circuitry is disposed in the housing and coupled to an electrode arrangement. The detection circuitry is configured to sense a cardiac electrical signal from the patient. A processor is coupled to the detection circuitry and configured to compute a first measure of heart rate variability (HRV) using the cardiac electrical signal, and compute a second measure of HRV using the cardiac electrical signal, the second measure of HRV differing from the first measure of HRV. The processor is also configured to produce an index of patient status derived from a ratio of the first and second measures of HRV, such that the index is a normalized HRV metric personalized to the patient. The processor or a remote system can use the index to assess acute and chronic changes in patient status.

20 Claims, 10 Drawing Sheets

(51) Int. Cl.
    *A61N 1/39*          (2006.01)
    *A61N 1/362*        (2006.01)
    *A61B 5/0205*       (2006.01)
    *A61B 5/0488*       (2006.01)
    *A61B 5/053*        (2006.01)
    *A61B 5/145*        (2006.01)
    *A61B 5/11*         (2006.01)
    *A61N 1/05*         (2006.01)

(52) U.S. Cl.
    CPC .............. *A61B 5/4833* (2013.01); *A61B 5/686* (2013.01); *A61B 5/6869* (2013.01); *A61N 1/0587* (2013.01)

(56) References Cited

U.S. PATENT DOCUMENTS

| | | | |
|---|---|---|---|
| 6,587,720 B2 | 7/2003 | Hsu et al. | |
| 6,731,974 B2 | 5/2004 | Levitan et al. | |
| 6,902,743 B1 | 6/2005 | Setterstrom | |
| 7,376,457 B2 | 5/2008 | Ross | |
| 7,480,528 B2 | 1/2009 | Brockway | |
| 7,580,745 B2 | 8/2009 | Pastore et al. | |
| 7,664,551 B2 | 2/2010 | Cigaina | |
| 7,672,725 B2 | 3/2010 | Pastore | |
| 7,899,527 B2 | 3/2011 | Yun | |
| 8,123,696 B2 | 2/2012 | Childre | |
| 8,170,668 B2 | 5/2012 | Ettori et al. | |
| 8,292,819 B2 | 10/2012 | Kuo et al. | |
| 8,394,029 B2 | 3/2013 | Lian | |
| 8,668,644 B2 | 3/2014 | Ong et al. | |
| 8,682,421 B2 | 3/2014 | Riftine | |
| 8,718,750 B2 | 5/2014 | Lian | |
| 8,768,469 B2 | 7/2014 | Tweden et al. | |
| 8,792,986 B2 | 7/2014 | Cigaina | |
| 8,831,724 B2 | 9/2014 | Pastore et al. | |
| 8,983,604 B2 | 3/2015 | Keel | |
| 2005/0095628 A1 | 5/2005 | Krempin et al. | |
| 2006/0020295 A1* | 1/2006 | Brockway | A61B 5/02405 607/17 |
| 2006/0074464 A1 | 4/2006 | Subera et al. | |
| 2013/0096395 A1 | 4/2013 | Katra et al. | |
| 2013/0209978 A1 | 8/2013 | Chen et al. | |

\* cited by examiner

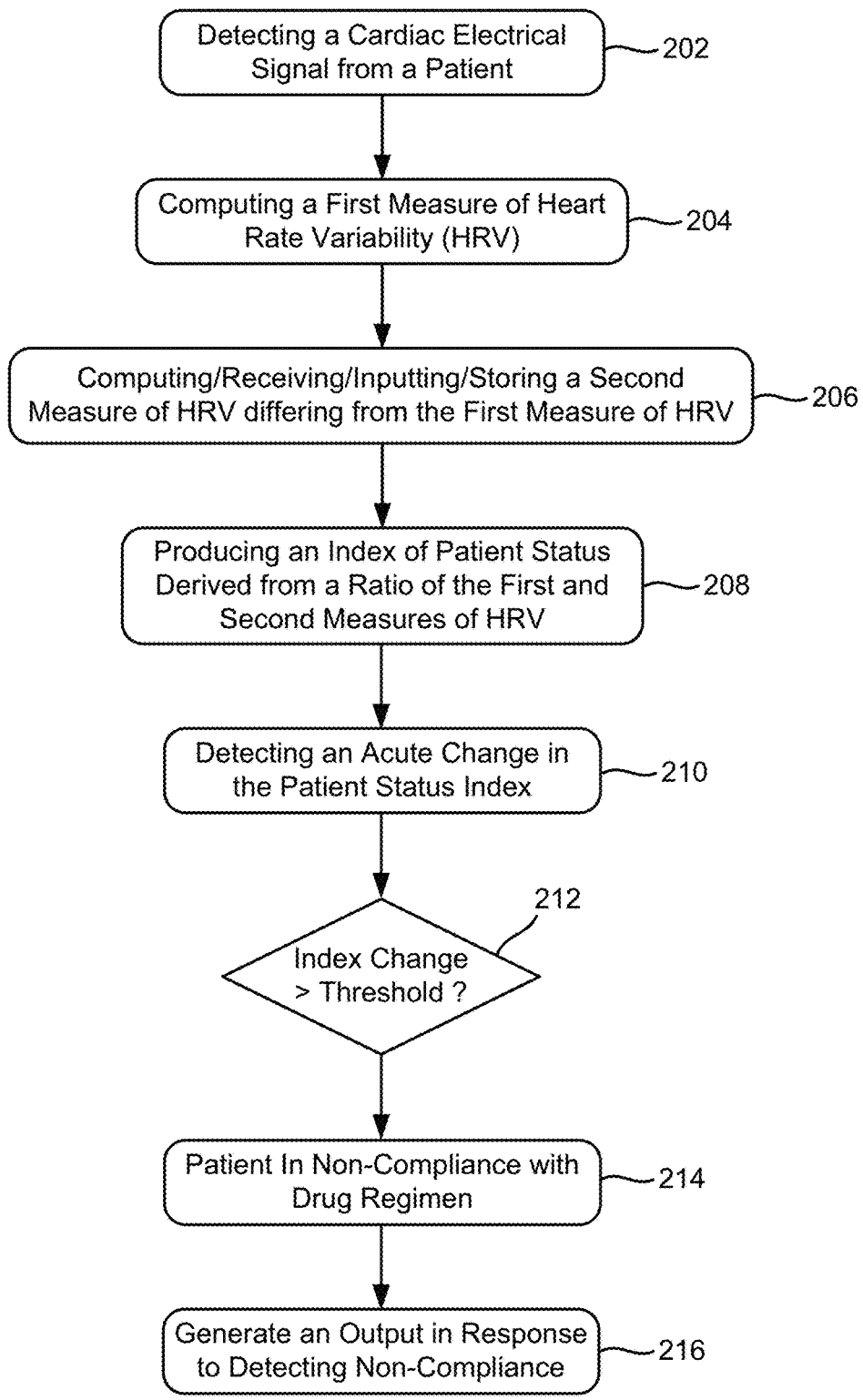

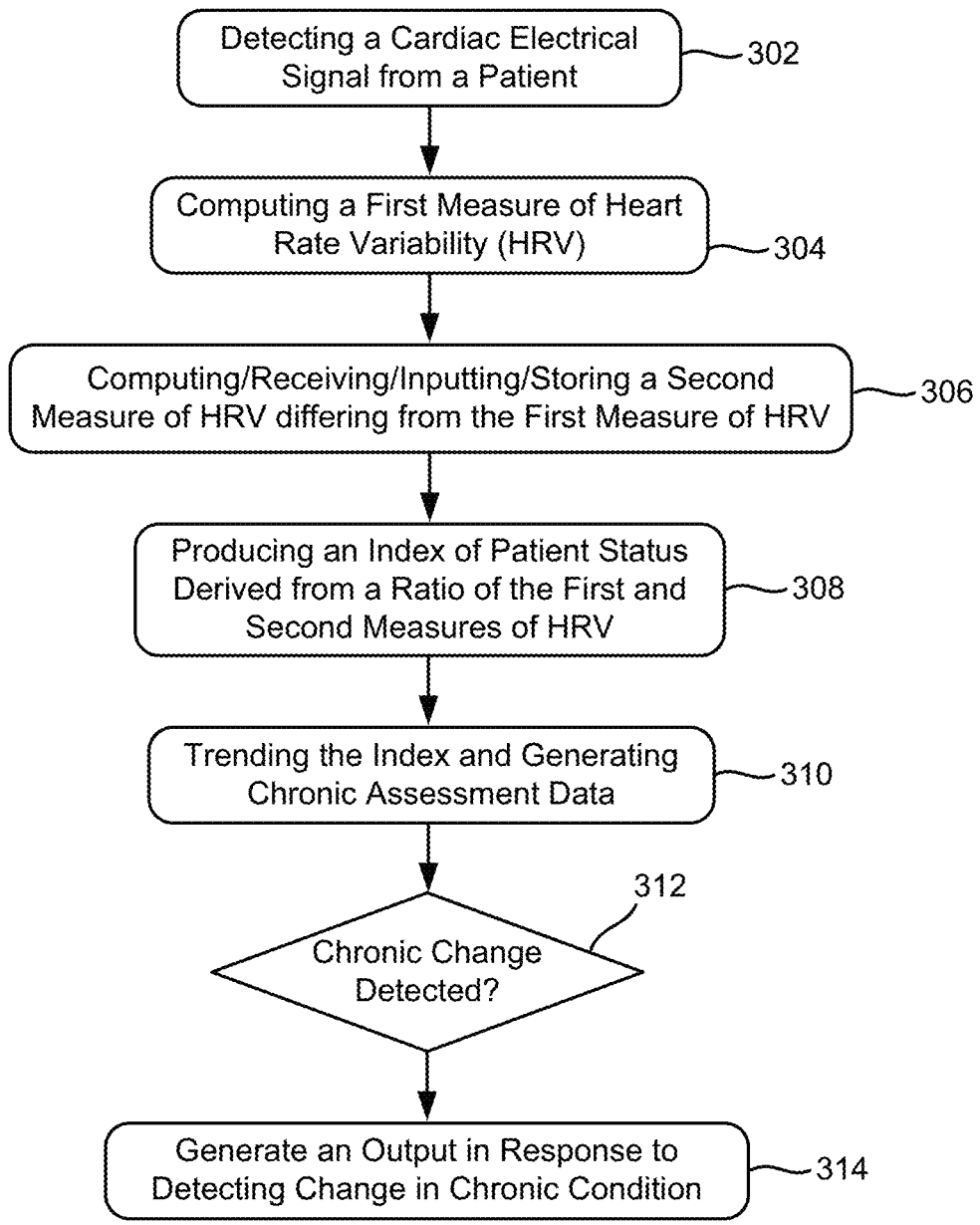

APPARATUS AND METHOD FOR PERSONALIZED CARDIAC SIGNAL PROCESSING

RELATED APPLICATIONS

This application claims the benefit of Provisional Patent Application Ser. No. 62/129,178, filed on Mar. 6, 2015, to which Applicant claims priority under 35 U.S.C. § 119(e), and which is incorporated herein by reference in its entirety.

TECHNICAL FIELD

This patent document pertains generally to cardiac signal monitoring and more particularly, but not by way of limitation, to systems and methods that assess patient status using a personalized index heart rate variability.

BACKGROUND

Electrical signals cause a heart to beat. In a healthy patient, regular heart beats pump blood through the cardiovascular system. The human cardiovascular system is responsible for receiving oxygen-deprived blood into the heart from the venous system of the body, delivering the oxygen-deprived blood to the lungs to be replenished with oxygen, receiving the oxygenated blood from the lungs back into the heart, and delivering the oxygenated blood to the body via the arterial vasculature. This process is regulated within the heart by electrical pulses that control the operation of the heart's receiving and pumping chambers.

In a healthy heart, the sinoatrial node of the heart generates electrical pulses in a consistent and regulated fashion to regulate receiving and pumping blood in the heart's chambers. The electrical impulses propagate as activation wavefronts across the atria, the upper chambers of the heart, and cause cells of the atria to depolarize and contract, which forces blood from the atria to the ventricles, the lower chambers of the heart. The ventricles receive the blood from the atria, and the wavefront, after passing through the atrioventricular node and moving to the Purkinje system, moves to cells of the ventricles causing the ventricles to contract and pump the blood to the lungs and to the rest of the body.

Various aspects of cardiac activity (e.g., heart rate, arrhythmias) can be detected by measuring, recording, and analyzing cardiac electrical signals, such as an electrocardiogram (ECG) signal. One way of measuring ECG signals involves attaching electrodes, typically ten, externally to a patient's skin and sensing the electrical signals that form the ECG waveform. Implantable monitoring systems can be implanted under the skin with electrodes that sense subcutaneous electrical signals, including ECG signals, which are analyzed as being indicative of cardiac activity.

Heart rate variability can be an important factor to consider when processing or otherwise using a cardiac signal. It is, in some instances, a measure of patient health and cardiac stability. For instance, it can be difficult to quantify how effectively a drug (such as, for instance, beta blockers) is regulating cardiac heart rate due to heart rate variability. In some instances, device-based atrial fibrillation (AF) detection involves measures of heart rate variability. Devices commonly use fixed variability ratios (i.e., 8%, 12%, or 18%); however, each patient has a unique variability that is modulated by a multitude of factors, such as age, gender, autonomic drive, disease severity, medication usage, etc. Therefore, what might be considered regular in one patient may be dangerously irregular in another.

SUMMARY

Embodiments of the disclosure are directed to methods and devices for producing a personalized index of patient status derived from a multiplicity of heart rate variability measurements in accordance with various embodiments. According to various embodiments, a method involves detecting a cardiac electrical signal from a patient, computing a first measure of heart rate variability (HRV) using the cardiac electrical signal, and computing a second measure of HRV using the cardiac electrical signal, the second measure of HRV differing from the first measure of HRV. The method also involves producing an index of patient status derived from a ratio of the first and second measures of HRV, such that the index is a normalized HRV metric personalized to the patient. The index can be used to assess acute and chronic changes in patient status.

According to other embodiments, a medical device includes a housing configured for implantation within a body of a patient. Detection circuitry is disposed in the housing and coupled to an electrode arrangement. The detection circuitry is configured to sense a cardiac electrical signal from the patient. A processor is coupled to the detection circuitry and configured to compute a first measure of heart rate variability (HRV) using the cardiac electrical signal, and compute a second measure of HRV using the cardiac electrical signal, the second measure of HRV differing from the first measure of HRV. The processor is also configured to produce an index of patient status derived from a ratio of the first and second measures of HRV, such that the index is a normalized HRV metric personalized to the patient. The processor or a remote system can use the index to assess acute and chronic changes in patient status.

The above summary is not intended to describe each disclosed embodiment or every implementation of the present disclosure. The figures and the detailed description below more particularly exemplify illustrative embodiments

BRIEF DESCRIPTION OF THE DRAWINGS

Throughout the specification reference is made to the appended drawings, where like reference numerals designate like elements, and wherein:

FIG. 2B is a flow chart illustrating various processes involving detection of acute changes in patient status resulting from non-compliance with a prescribed drug regimen in accordance with various embodiments;

FIG. 3 is a flow chart illustrating various processes involving detection of chronic changes in patient status in accordance with various embodiments;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

The present inventor has recognized, among other things, that accounting for individual heart rate variability can be important when processing or otherwise using a cardiac signal. The present inventor has recognized that it is desirable to provide an apparatus or method for personalized cardiac signal processing.

In the following detailed description, reference is made to the accompanying drawing which form a part hereof, and in which is shown by way of illustration specific examples in which the present description may be practiced. These examples are described in sufficient detail to enable those skilled in the art to practice the present subject matter, and it is to be understood that other examples may be utilized and that structural changes may be made without departing from the scope of the present description. Therefore, the following detailed description is not to be taken in a limiting sense.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, or process that includes elements in addition to those listed after such a term are still deemed to fall within the scope of the description. Moreover, the terms "first," "second," and "third," etc. are used merely as labels, and are not intended to impose numerical requirements on their objects.

Figure 1:
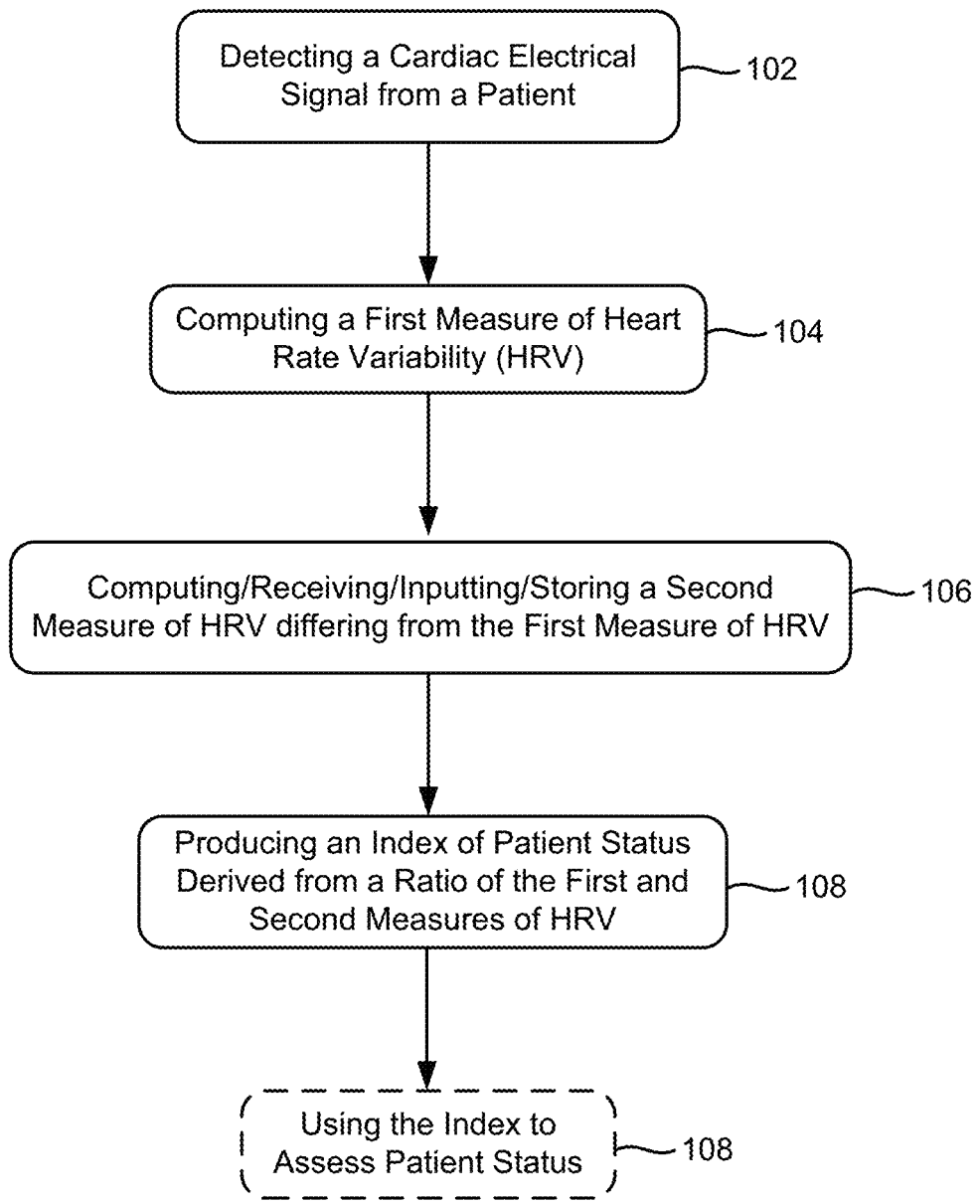
FIG. 1 is a flow chart illustrating various processes for producing a personalized index of patient status derived from a multiplicity of heart rate variability measurements in accordance with various embodiments.

FIG. 1 is a flow chart illustrating various processes for producing a personalized index of patient status derived from a multiplicity of heart rate variability measurements in accordance with various embodiments. The method illustrated in FIG. 1 involves detecting 102 of cardiac electrical signal from a patient, and computing 104 a first measure of HRV. The method also involves computing, receiving, inputting or storing 106 a second measure of HRV differing from the first HRV measure. In some embodiments, the second HRV measure is computed and stored in a memory of a medical device or an external system, and subsequently retrieved from memory when calculating an HRV index. In other embodiments, the second HRV measure is input by a healthcare professional and used when calculating an HRV index. The method further involves producing 108 an index of patient status derived from a ratio of the first and second measures of HRV. The method may also involve using the index to assess 108 patient status.

According to various embodiments, an index of patient status is derived from a ratio of a first measure of HRV and a second measure of HRV, such that the index is a normalized HRV metric personalized to the patient. The index can be expressed as:

$$\frac{HRV_1}{HRV_2}$$

where $HRV_1$ and $HRV_2$ are different measures of HRV. An HRV measure can be stored and, if applicable, updated (and stored again) over time for use as the denominator of a ratio of HRV measures for normalization or personalization. This stored HRV measure, indicated as $HRV_2$ in the index above, can be an HRV measure of a type discussed herein or can be an input from or supplied by a healthcare professional based, for example, on a population-based HRV or equivalent.

In the index above, $HRV_1$ and $HRV_2$ can be any of the following representative HRV measures:

- an instantaneous measure of the patient's HRV ($HRV_i$);
- a measure of the patient's HRV at a baseline heart rate ($HRV_{baseline\ HR}$);
- a measure of the patient's HRV at peak heart rate ($HRV_{peak\ HR}$);
- a daytime measure of the patient's HRV ($HRV_{day}$);
- a nighttime measure of the patient's HRV ($HRV_{night}$);
- the patient's HRV at a prescribed time of day ($HRV_{time}$);
- the patient's HRV over a predetermined duration of time ($HRV_{fixed\ time}$);
- an adaptive measure of the patient's HRV ($HRV_{adaptive}$);
- a maximum measure of the patient's HRV ($HRV_{max}$);
- a minimum measure of the patient's HRV ($HRV_{min}$);
- a measure of the patient's HRV during a period of high patient activity ($HRV_{high\ activity}$); and
- a measure of the patient's HRV during a period of low patient activity ($HRV_{low\ activity}$).

The HRV measures listed above are illustrative, non-limiting examples that can be used to develop an index that is personalized to the patient. In some embodiments, one of the numerator and the denominator of a ratio of HRV measures is an HRV measure personalized to the patient. The other of the numerator and denominator can be a non-personalized HRV measure or a value of HRV computed using conventional approaches (e.g., DNN, SDNN, etc.), examples of which are discussed hereinbelow. In other embodiments, both the numerator and the denominator of a ratio of HRV measures is an HRV measure personalized to the patient. Some indices derived from a ratio of different HRV measures are unitless (e.g., two HRV measures given in terms of time of day), while other indices are expressed in terms of units (e.g., an HRV measure expressed in terms of time and an HRV measure expressed in terms of frequency).

According to various embodiments disclosed herein, HRV can be computed using a known approach, such as computing DNN or SDNN, which is the standard deviation of NN (normal beat) intervals, often calculated over a 24-hour period. Another approach involves computing SDANN, which is the standard deviation of the average NN intervals calculated over short periods, typically 5 minutes. HRV can be computed using RMSSD (root mean square of successive differences), which is the square root of the mean of the squares of the successive differences between adjacent NNs. Another approach involves computing SDSD (standard deviation of successive differences), which is the standard deviation of the successive differences between adjacent NNs. A further approach involves computing NN50, which is the number of pairs of successive NNs that differ by more than 50 ms. Computing pNN50 is another approach, which involves calculating the proportion of NN50 divided by total number of NNs. NN20 can also be used, which is the number of pairs of successive NNs that differ by more than 20 ms, as can pNN20, which is the proportion of NN20 divided by total number of NNs.

EBC (estimated breath cycle) is another approach, which involves computing the range (max-min) within a moving window of a given time duration within the study period. The windows can move in a self-overlapping way or be strictly distinct (sequential) windows. EBC can be used where HRV feedback in real-time is a primary goal. Other approaches are often referred to as geometric methods, in which the series of NN intervals are converted into a geometric pattern such as the sample density distribution of NN interval durations, sample density distribution of differences between adjacent NN intervals, Lorenz plot of NN or RR intervals, and the like. A simple formula is used that judges the variability on the basis of the geometric and/or graphics properties of the resulting pattern. Frequency domain approaches can also be used, such as methods that assign bands of frequency and then count the number of NN intervals that match each band. The bands are typically high frequency (HF) from 0.15 to 0.4 Hz, low frequency (LF) from 0.04 to 0.15 Hz, and the very low frequency (VLF) from 0.0033 to 0.04 Hz. Power spectral density (PSD) represents a further approach to computing HRV, and uses parametric or nonparametric methods to provide basic information on the power distribution across frequencies. A commonly used PSD method involves use of the discrete Fourier transform (DFT). A more recent approach involves use of an HRV metric that depends on wavelet entropy measures. More exotic approaches include non-linear methods, such as methods that use a Poincaré plot.

Of the various ratios of HRV measures, the following are non-limiting examples that may be particularly useful for assessing acute and chronic patient conditions and status:

$$\frac{HRV_{day}}{HRV_{night}}$$

where $HRV_{day}$ is a measure of the patient's average daytime HRV, and $HRV_{night}$ is a measure of the patient's average nighttime HRV. This HRV metric is useful for assessing the daily dynamic range of HRV for a given patient. The index will reflect the daily HRV for a patient based on their unique cardiac characteristics and disease conditions, benchmarked to the patient's nightly HRV, considered to be the period of lowest autonomic drive.

$$\frac{HRV_{day}}{HRV_{mean}}$$

where $HRV_{day}$ is a measure of the patient's average daytime HRV as indicated above, and $HRV_{mean}$ is a measure of the patient's mean HRV. This index will reflect the daytime HRV for a patient, benchmarked to the patient's nominal HRV over an average time period that can span, for example, hours, days, weeks, or longer.

$$\frac{HRV_{max}}{HRV_{min}}$$

where $HRV_{max}$ is a measure of the patient's maximum HRV, and $HRV_{min}$ is a measure of the patient's minimum HRV. This HRV metric is useful for assessing the maximum dynamic range of HRV for a given patient, based on their unique cardiac characteristics and disease conditions.

$$\frac{HRV_{fixed\ time}}{HRV_{time}}$$

where $HRV_{fixed\ time}$ is a measure of the patient's HRV at a specified time of day or night, and $HRV_{time}$ is a measure of the patient's HRV at a desired or arbitrary time, such as time of patient assessment in a physician's office.

$$\frac{HRV_i}{HRV_b}$$

where $HRV_i$ is a measure of the patient's instantaneous HRV, and $HRV_b$ can be a measure of the patient's HRV at a specified or arbitrary time, a baseline measure of HRV, a measure of HRV during a physiologic episode (e.g., arrhythmia) or a measure of HRV during the efficacy period of a drug (e.g., a prescribed pharmacological substance).

$$\frac{HRV_{patient}}{HRV_{population}}$$

where $HRV_{patient}$ is a measure of the patient's HRV normalized to $HRV_{population}$, the measure of HRV for a specified or generalized population of patients with comparable demographics, characteristics, disease conditions, etc.

$$\frac{HRV_i}{HRV_{adaptive}}$$

where $HRV_i$ is a measure of the patient's instantaneous HRV, and $HRV_{adaptive}$ is a measure of the patient's HRV computed over time, such as a learned HRV developed from histograms and/or trending of the patient's HRV over time. For example, an adaptive measure of a patient's HRV can be reflective of the patient's HRV as it changes due to changes in the severity of disease condition or medication changes, for example.

$$\frac{HRV_{hi\ activity}}{HRV_{low\ activity}}$$

where $HRV_{hi}$ activity is a measure of HRV computed during periods of high activity of the patient, such as determined by use of an accelerometer, and $HRV_{low\ activity}$ is a measure of HRV computed for periods of low patient activity, which can also be determined using an accelerometer. This HRV metric is useful for assessing the dynamic range of HRV for a given patient, as a function of their activities of daily living.

$$\frac{HRV_{peak\ HR}}{HRV_{baseline\ HR}}$$

where $HRV_{peak\ HR}$ is a measure of HRV computed during periods of peak heart rate and $HRV_{baseline\ HR}$ is a measure of HRV computed for periods of nominal resting heart rate. This metric is useful for assessing the patient's HRV at arrhythmogenic heart rates or vigorous exercise, benchmarked to their HRV values during normal cardiac rhythm or at rest, for example.

According to various embodiments, a personalized index of patient status derived from a multiplicity of HRV measurements can be used to detect acute changes in a patient's status. Examples of acute changes in a patient's status include changes due to compliance or noncompliance with a drug regimen prescribed by a physician or changes due to a change in clinical status. An acute change in patient status is a physiological change that occurs over a relatively short period of time, such as on the order of minutes to several hours (e.g., 30 minutes-2 hours, 1-4 hours), but typically less than one day. For example, an acute change in patient status can be detected as a physiological response to missing a scheduled dosage of beta blockers or other drug, which can be detected according to various embodiments of the present disclosure.

It is often difficult to quantify how to effectively titrate a drug, quantify its efficacy, or gauge patient compliance with a specific medication regimen, such as with beta blockers which regulate heart rate. This can be due to, at least in part, normal fluctuations in heart rate variability during the day and/or as a result of physical/emotional stressors and physical activity levels. Heart rate is least variable during calm periods of sleep. According to some embodiments, by normalizing a patient's peak heart rate variability during wakeful hours by the patient's lowest heart rate variability during sleep, a personalized score for heart rate variability can be generated for the patient, which can be represented by the following personalized index of patient status:

$$\frac{HRV_{wakeful\ peak\ HR}}{HRV_{sleeptime\ minimum}}$$

This index of patient status can be monitored chronically to determine, for instance, how effectively a medication is regulating the heart rate variability and/or how compliant a patient is in adhering to a prescribed drug regimen.

Figure 2A:
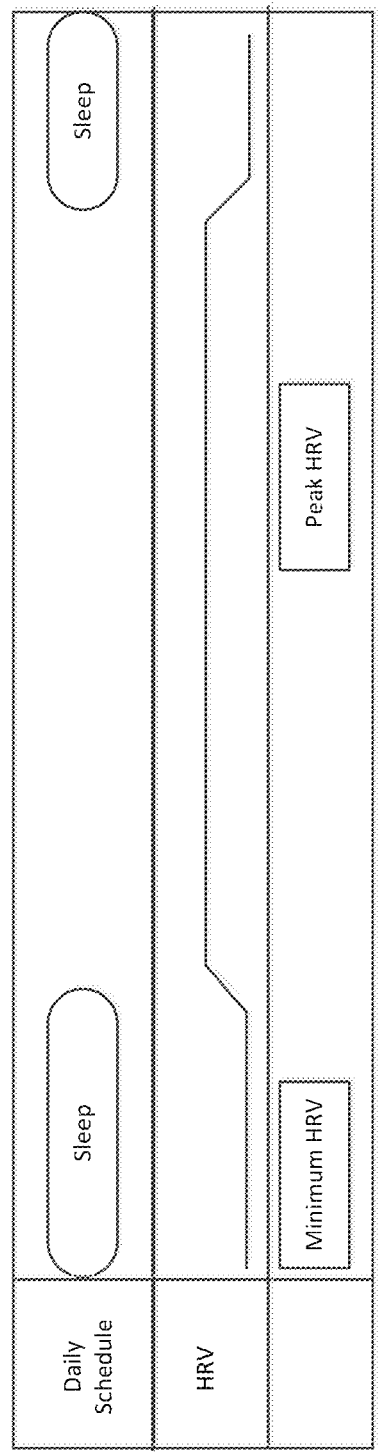
FIG. 2A is a diagram illustrating circadian/activity-based changes to a patient's cardiac variability over the course of a daily schedule in accordance with various embodiments.

With reference to FIG. 2A, circadian/activity-based changes can be seen in cardiac variability. During sleep, cardiac variability tends to be at its lowest for a given patient. During wakeful hours, heart rate variability tends to increase. Some embodiments can use the ratio of $HRV_{max}$ to $HRV_{min}$ as a performance metric. Increases or decreases in this ratio over time can be correlated to increased or decreased efficacy of pharmaceutical therapy or improvement or worsening of the underlying disease condition.

In various embodiments, an apparatus, system, method, and/or algorithm can use $HRV_{mean}$ vs. $HRV_{nocturnal}$ for medicine management (e.g., a beta-blocker). In some embodiments, the apparatus, system, method, and/or algorithm can measure efficacy of an anti-arrhythmia drug by monitoring $HRV_{peak}$ vs. $HRV_{min}$. In other embodiments, the apparatus, system, method, and/or algorithm can use an average HRV collected at night when the patient is believed to be asleep or minimally active and compare this measure of $HRV_{night/lo\ activity}$ to that of the daily HRV, $HRV_{day}$. In some embodiments, $HRV_{peak}$ or $HRV_{mean}$ during the day can be used. In other embodiments, RR, delta RR, SDNN, or the like can be used instead of or in addition to basic HRV. In some embodiments, nocturnal detection around a fixed time/schedule, such as, for instance, 3:00 AM, can be used.

In further embodiments, detection can be coupled to a three-dimensional accelerometer to assess periods of lowest activity. The detection can be made in real-time or in retrospective offline analysis of patient data. The detection thresholds, in various embodiments, can be automated and/or can be entered manually by a healthcare provider. The thresholds for abnormal HRV detection (i.e., the limits of detection) can be, in some embodiments, derived from an adaptive algorithm that tracks patient unique HRV behavior over time or, in other embodiments, can be based on a preset cut-off associated with abnormal HRV response. These and other similar approaches provide for a personalized normalized HRV score that can be derived and used for monitoring medication efficacy.

The embodiment illustrated in FIG. 2B is directed to detecting acute changes in patient status resulting from non-compliance with a prescribed drug regimen, and involves detecting 202 a cardiac electrical signal (e.g., ECG or EGM) from the patient. The method shown in FIG. 2B involves computing 204 a first measure of HRV, and computing, receiving, inputting or storing 206 a second measure of HRV differing from the first HRV measure. In some embodiments, the second HRV measure is computed and stored in a memory of a medical device or an external system, and subsequently retrieved from memory when calculating an HRV index. In other embodiments, the second HRV measure is input by a healthcare professional and used when calculating an HRV index. An index of patient status is derived 208 from a ratio of the first and second measures of HRV. The method involves detecting 210 an acute change in the patient status index, and comparing 212 the acute change to a threshold. The threshold can be established and adjusted depending on the physiologic condition or parameter being assessed and the particular index being used to detect the acute change.

If it is determined that the acute change in the patient status index is greater than the threshold, the patient is considered to be in non-compliance 214 with the drug regimen. An output can be generated 216 in response to detecting non-compliance with the drug regimen. If the change 210 is less than the index change threshold 212, the system would revert to detecting a new cardiac signal 202 and computing a new first measure of HRV 204. For example, the processes illustrated in FIG. 2B can be implemented by an implantable medical device which communicates wirelessly with a handheld computing device in the patient's possession. The output indicative of non-compliance with the drug regimen can be communicated from the implantable device to the handheld computing device, which may generate an alert (audio and/or visual) that is perceivable to the patient. The alert may include a message (presented on a display of the device) indicating that a prescribed medication has not been taken or reminding the patient to take the prescribed medication. In some embodiments, the output indicative of non-compliance with the drug regimen can be transmitted to a remote system, which can be accessed by the patient's physician or medical provider. The physician or medical provider can recommend remedial action, such as contacting the patient or the patient's caregiver via a phone call, text, email or a message sent from the server back to the handheld computing device.

In accordance with some embodiments, a personalized index of patient status derived from a multiplicity of HRV measurements can be used to detect chronic changes in a patient's status. Examples of chronic changes in a patient's status include those associated with the cardiovascular system, pulmonary system, and/or the nervous system. Specific chronic changes in a patient's status that may be of interest include cardiovascular disease (e.g., chronic heart failure, myocardial dysfunction, AF), pulmonary disease (e.g., chronic obstructive pulmonary disease), and peripheral neuropathy (e.g., diabetic neuropathy). A chronic change in patient status is a physiological change that occurs over a relatively long period of time, such as on the order of weeks, months, or even years, but typically not less than about a month (less than one month is the acute regime).

The method shown in FIG. 3 involves detecting 302 a cardiac electrical signal from the patient, computing 304 a first measure of HRV, and computing, receiving, inputting or storing 306 a second measure of HRV differing from the first HRV measure. In some embodiments, the second HRV measure is computed and stored in a memory of a medical device or an external system, and subsequently retrieved from memory when calculating an HRV index. In other embodiments, the second HRV measure is input by a healthcare professional and used when calculating an HRV index. The method also involves producing 308 and index of patient status derived from a ratio of the first and second measures of HRV. The method further involves trending 310 the index over relatively long period of time and generating chronic assessment data. A chronic change in the patient's status can be detected 312 using the chronic assessment data, such as by detecting a change that exceeds a predetermined threshold. The threshold can vary depending on the physiologic condition or parameter being assessed in the particular index being used to detect the chronic change. The threshold for change detection can be a pre-specified fixed value that would be preset by a healthcare provider, or can be adaptive in nature where the adaptation is based on the data derived from the chronic values of the ratio index. An output can be generated 314 in response to detecting a change in the chronic condition of the patient. In response to detecting a chronic change in the patient's status, and alert message may be generated and transmitted to one or both of the patient and the patient's physician as discussed previously.

Atrial fibrillation together with atrial flutter is considered the most commonly sustained arrhythmia found in clinical practice. Atrial fibrillation (AF) involves rapid and chaotic beating of the individual fibers of the heart muscle such that synchronous contraction is not maintained. This inevitably results in that part of the heart ceasing to pump blood, which in turn can lead to embolic stroke. Atrial fibrillation is characterized by the presence of multiple reentrant circuits that may be active simultaneously, precluding the synchronous activation of enough atrial myocardium to generate an identifiable p-wave or coordinated atrial contraction. While not fatal on its own, AF may in turn lead to a fatal arrhythmia involving the ventricles. AF is often treated with medication to slow the heart rate to a near normal range or to convert the rhythm to normal sinus rhythm. Some implantable medical devices are configured to deliver electrical cardioversion therapy to convert AF to normal sinus rhythm.

Device-based atrial fibrillation detection often involves measures of heart rate or beat-to-beat variability. Devices commonly use fixed variability ratios (i.e., 8%, 12%, or 18%). However this fixed one-size-fits-all threshold approach lacks the sensitivity and specificity for detection of AF since each patient has a unique cardiac variability and what might be considered regular in one patient may be dangerously irregular in another. In some embodiments, by recording a historical average of heart rate variability and adaptively adjusting device variability thresholds for atrial fibrillation, more accurate reporting or therapeutics for atrial fibrillation can be delivered.

In some embodiments, an apparatus, system, method, and/or algorithm adaptively changes a threshold for heart rate variability. For example, the apparatus, system, method, and/or algorithm can be configured to derive a personalized ratio of HRV ($HRV_1/HRV_2$) to gauge and autotune AF detection sensitivity and specificity. In some embodiments, a similar apparatus, system, method, and/or algorithm can be used for detecting and/or treating tachycardia and/or bradycardia rhythms of the ventricles.

In various embodiments, the apparatus, system, method, and/or algorithm can use a personalized HRV value that is derived from the patients themselves based on their own unique condition and variations in rhythm, instead of using a fixed cut-off of detection (e.g., X % or Y %). In some embodiments, $HR_{max}$ and $HR_{min}$ or the like can be used. According to various embodiments, an apparatus, system, method, and/or algorithm can use a standard deviation from a mean value of zone of values around a histogram. In some embodiments, outlier detection or the like can be used. An apparatus, system, method, and/or algorithm, in some embodiments, can dynamically track patient-derived data over time and create a zone of values (i.e., a safe zone) around the patient-derived data that are considered normal. As newly collected data deviates outside the "safe zone," in some embodiments, an abnormal event detection can be made for the AF, tachycardia, or bradycardia. In this way, the criteria for arrhythmia detection are not arbitrarily fixed, but rather able to track the patient's unique characteristics and the uniqueness of the disease progression chronically in the patient.

Figure 4:
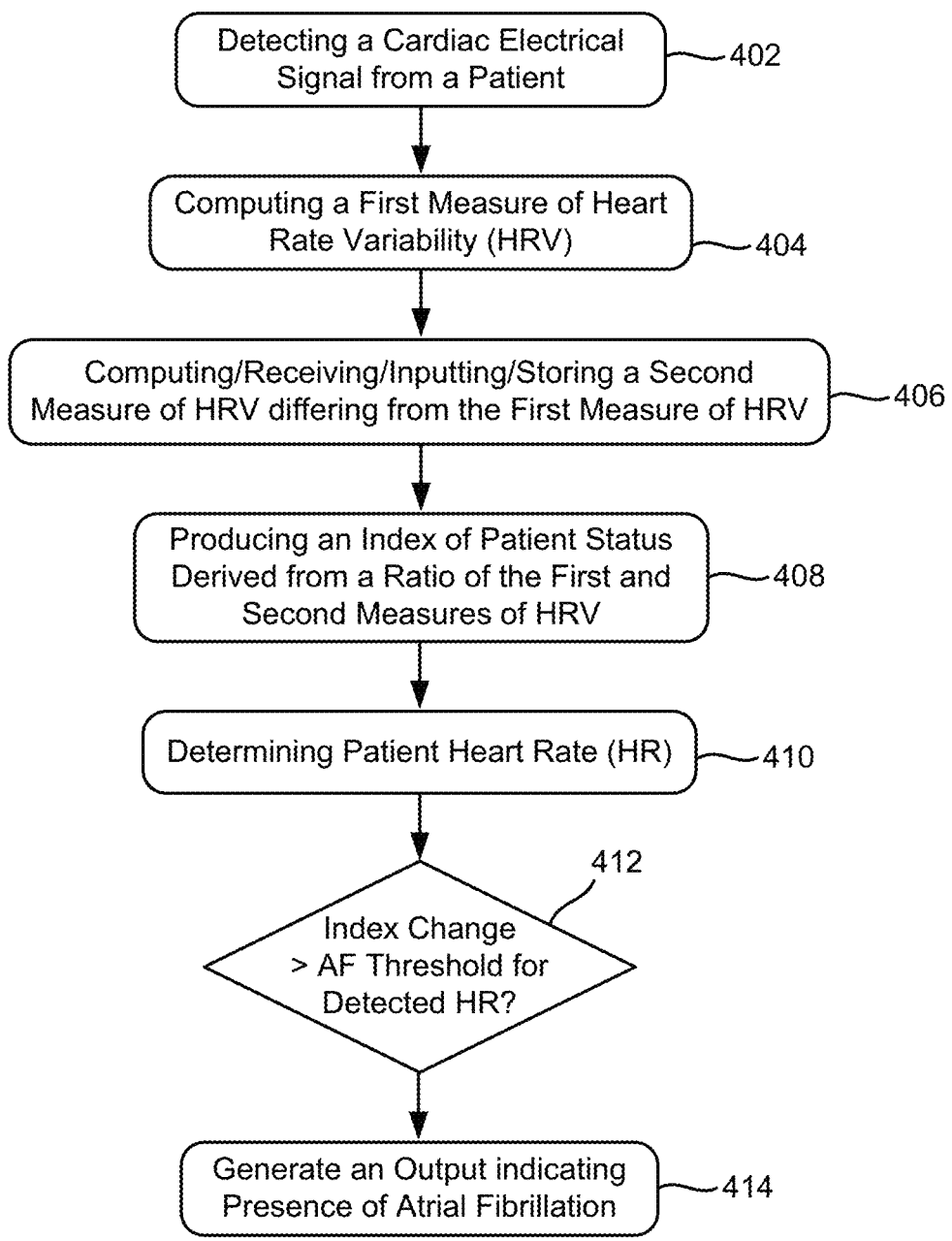
FIG. 4 is a flow chart illustrating various processes for detecting atrial fibrillation in accordance with various embodiments.

FIG. 4 is a flow chart illustrating various processes for detecting atrial fibrillation in accordance with various embodiments. The method shown in FIG. 4 involves detecting 402 a cardiac electrical signal from the patient, computing 404 a first measure of HRV, and computing, receiving, inputting or storing 406 a second measure of HRV differing from the first HRV measure. In some embodiments, the second HRV measure is computed and stored in a memory of a medical device or an external system, and subsequently retrieved from memory when calculating an HRV index. In other embodiments, the second HRV measure is input by a healthcare professional and used when calculating an HRV index. An index of patient status is produced 408 from a ratio of the first and second measures of HRV. For example, the ratio of first and second HRV measures can include an HRV measure that is personal to the patient, such that the index of patient status is given by the ratio $HRV_1/HRV_2$, where $HRV_1$ in the numerator can be any measure of HRV and $HRV_2$ is any second measure of HRV different than the first HRV measure, thereby resulting in a personalized (individualized or unique) ratio status index to the patient.

Using the detected cardiac electrical signal, the patient's heart rate (HR) is determined 410. The index of patient status is monitored for changes that exceed a predetermined AF threshold for the patient's detected heart rate. If the change in the index is greater than the threshold for the patient's detected heart rate 412, and output is generated 414 indicating presence of atrial fibrillation. As was discussed previously, an alert can be generated and transmitted to one or both of the patient and the patient's healthcare provider in response to detection of atrial fibrillation.

Figure 5:
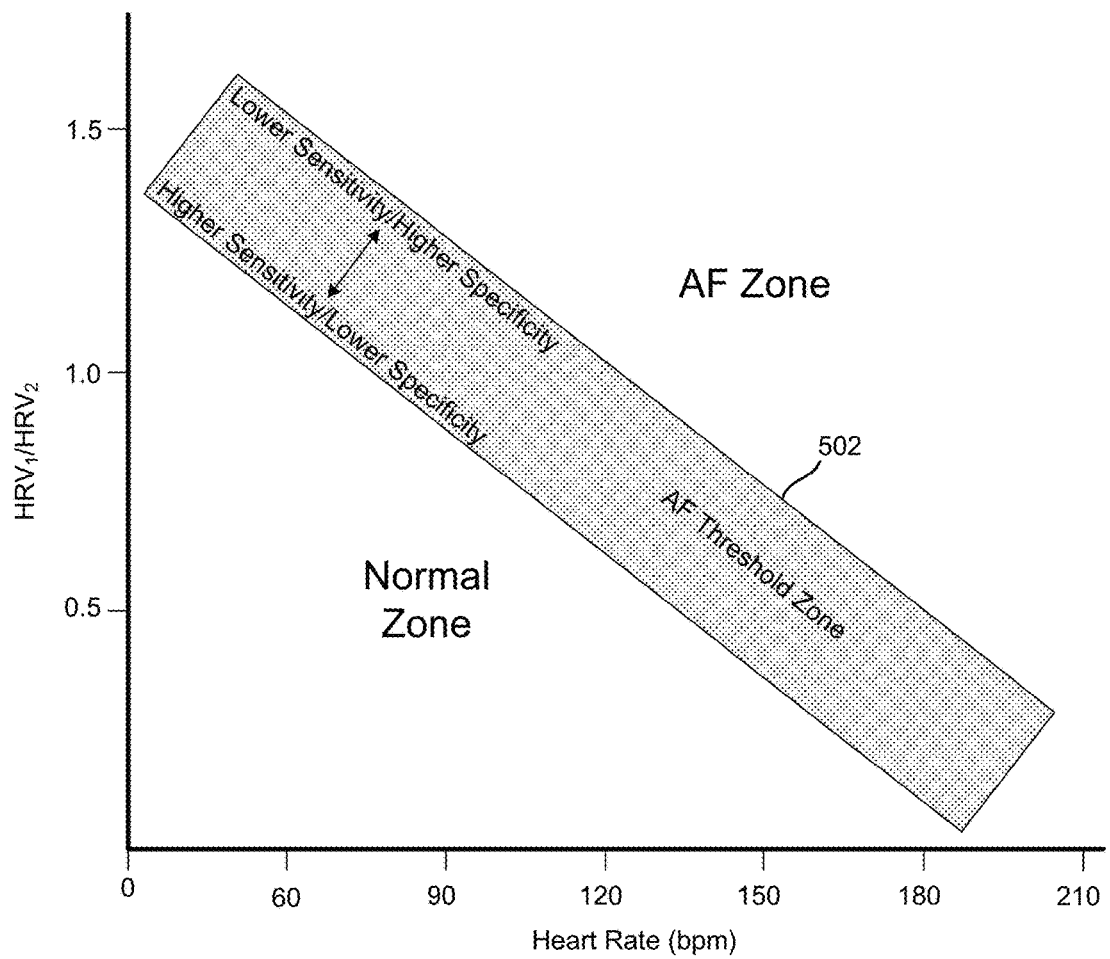
FIG. 5 illustrates an AF threshold zone that demarcates a normal zone from an AF zone tailored to a particular patient in accordance with various embodiments.

FIG. 5 illustrates an AF threshold zone 502 that demarcates a normal zone from an AF zone for a particular patient. The y-axis of the graph shown in FIG. 5 represents an index of patient status given by a ratio of first and second measures of HRV (e.g., $HRV_1/HRV_2$). The x-axis represents heart rate given in beats per minute (bpm). It can be seen in FIG. 5 that, at low heart rates, the AF zone is reached at relatively high HRV ratios. It can also be seen in FIG. 5 that, at elevated heart rates, the AF zone can be reached at relatively low HRV ratios. The AF threshold zone 502 shown in FIG. 5 was developed in recognition of the physiologic relationship between HRV and heart rate, in that the range of normal HRV index values is relatively large at low heart rates and relatively small at high hear rates.

In the embodiment shown in FIG. 5, the threshold demarcating the AF zone from the normal zone is given as an AF threshold zone 502, rather than a single line or curve. An AF threshold line or curve can be selected or defined by the physician or algorithmically by a medical device (e.g., an implantable loop recorder or anti-arrhythmia therapy device) in order to achieve a desired level of sensitivity and specificity. For the AF threshold zone 502 shown in FIG. 5, an AF threshold line or curve biased toward the graph's origin (0, 0) serves to provide higher sensitivity and lower specificity for detecting AF. An AF threshold line or curve biased away from the graph's origin serves to provide lower sensitivity and higher specificity for detecting AF. Accordingly, the AF threshold line or curve can be tailored by the physician or algorithmically by a medical device to achieve a desired level of sensitivity and specificity for detecting AF for a particular patient. For example, and as discussed previously, a historical average of heart rate variability for a patient can be recorded and the medical device can be configured to adaptively adjust cardiac variability thresholds for atrial fibrillation detection, thereby providing for more accurate delivery of atrial fibrillation therapy.

It is noted that the y-axis scale and units in FIG. 5 are arbitrary in this illustrative example and can be different than what is presented depending on the ratio of $HRV_1$ to $HRV_2$ that is chosen. It is also noted that the x-axis being HR is a good variable for correlation with HRV ratio, but other variables could be used, such as patient age, activity level, severity of disease condition, BMI, etc.

Figure 6:
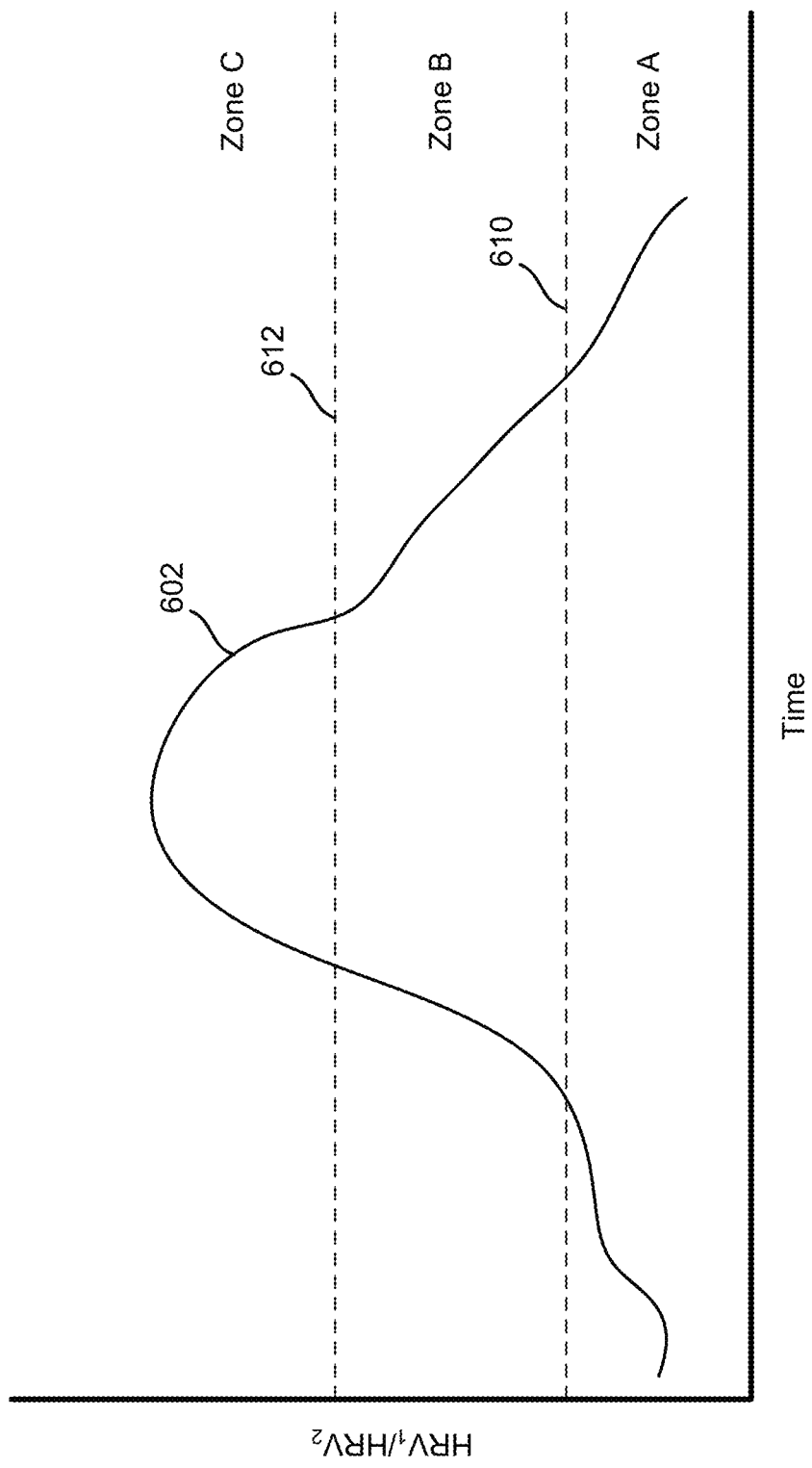
FIG. 6 is a graph showing a change in an index of patient status given by a ratio of HRV measures in accordance with various embodiments.

FIG. 6 is a graph showing a change in an index 602 of patient status given by a ratio of HRV measures ($HRV_1/HRV_2$) in accordance with various embodiments. The plot of index 602 shown in FIG. 6 can be illustrative of acute changes or chronic changes in the index 602 as a function of time. Three zones (A, B, and C) are shown, whereby a first threshold 610 demarcates zone A from zone B, and a second threshold 612 demarcates zone B from zone C. According to the illustrative embodiment shown in FIG. 6, zone A represents a zone where the index 602 indicates that the patient status is good or acceptable, and therefore is not of concern. Zone B represents a zone where the index 602 indicates that the patient status is poor, and therefore is of concern. Zone C represents a zone where the index 602 indicates that the patient status is critical, and therefore is of heightened or immediate concern.

A patient status monitoring methodology according to various embodiments involves detecting if and when the index 602 exceeds or falls below a zone threshold 610 or 612 over time. When a given zone threshold 610 or 612 is crossed, an appropriate alert can be generated and reported to the patient and/or the patient's physician. For example, the monitoring methodology may detect that the index 602 crosses the first threshold 610 when moving from zone A to zone B, thereby indicating deterioration in patient status. Improvement in patient status can be detected by the index 602 crossing the first threshold 610 when moving from zone B to zone A. Similarly, the monitoring methodology may detect that the index 602 crosses the second threshold 612 when moving from zone B to zone C, thereby indicating significant deterioration in patient status, while improvement in patient status can be detected by the index 602 crossing the second threshold 612 when moving from zone C to zone B. Note that while thresholds 610 and 612 are illustrated in FIG. 6 as being fixed over time in this example, it is anticipated in another embodiment to be adaptive thresholds that change over time in response to changes in the patient's index 602.

Figure 7:
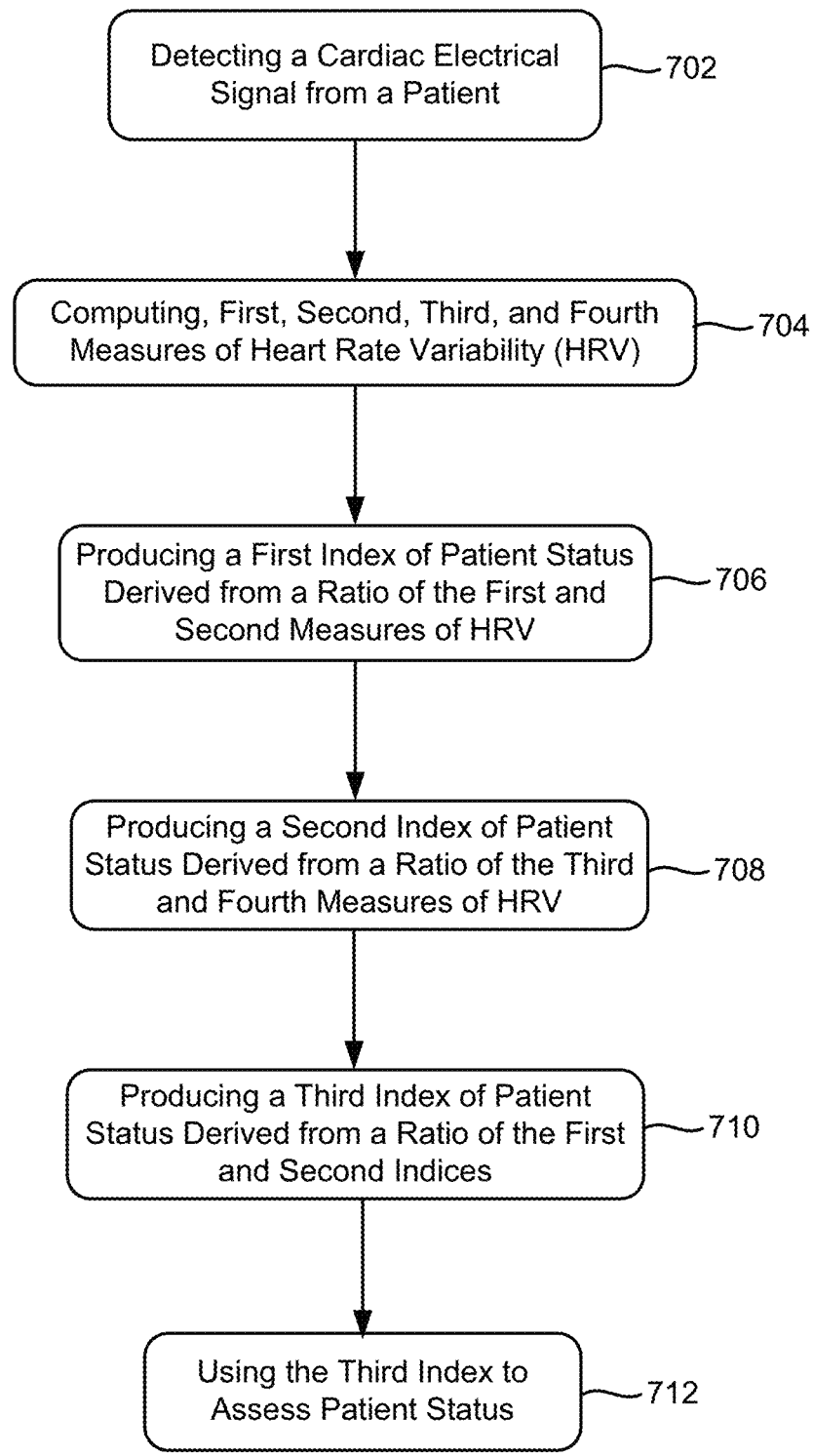
FIG. 7 is a flow chart illustrating various processes involving use of multiple HRV indices that provide for enhanced diagnostic power and/or to indicate different clinical situations in accordance with various embodiments.

Some embodiments of the present disclosure are directed to the use of multiple HRV indices that provide for enhanced diagnostic power and/or to indicate different clinical situations. The methodology shown in FIG. 7 involves detecting 702 a cardiac electrical signal from a patient, and computing first, second, third, and fourth measures of HRV, each of which is distinct. The methodology involves producing 706 a first index of patient status derived from a ratio of the first and second HRV measures, and producing 708 a second index of patient status derived from a ratio of the third and fourth HRV measures. For example, the first index, $I_1$, and the second index, $I_2$, can be given as:

$$I_1 = \frac{HRV_1}{HRV_2}$$

and $$I_2 = \frac{HRV_3}{HRV_4}.$$

A third index of patient status, $I_3$, can be derived 710 from a ratio of the first and second indices, $I_1$ and $I_2$, as follows:

$$I_3 = \frac{I_1}{I_2}.$$

The patient's third status index, $I_3$, can be used 712 to assess patient status.

In some embodiments, different patient status indices (e.g., $I_1$ and $I_2$) can be compared to each other. In some cases, a comparison of two or more status indices can be assessed to determine whether the different indices are in agreement or in discordance when assessing patient status. For example, a second index (e.g., $I_2$) may be used to confirm the detection of the first index (e.g., $I_1$). Use of multiple patient status indices can be used to increase the sensitivity and specificity of detection. In some cases, a comparison of $I_1$ and $I_2$ may reveal that the two indices are in agreement or in discordance. If discordant, further assessment of the patient status may be in order. For example, atrial fibrillation can be detected using a comparison of the first and second indices, $I_1$ and $I_2$, wherein the agreement of the two indices serves as a confirmatory result and a lack of agreement of the 2 indices serves as an indicator prompting additional analysis for atrial fibrillation detection.

Figure 8:
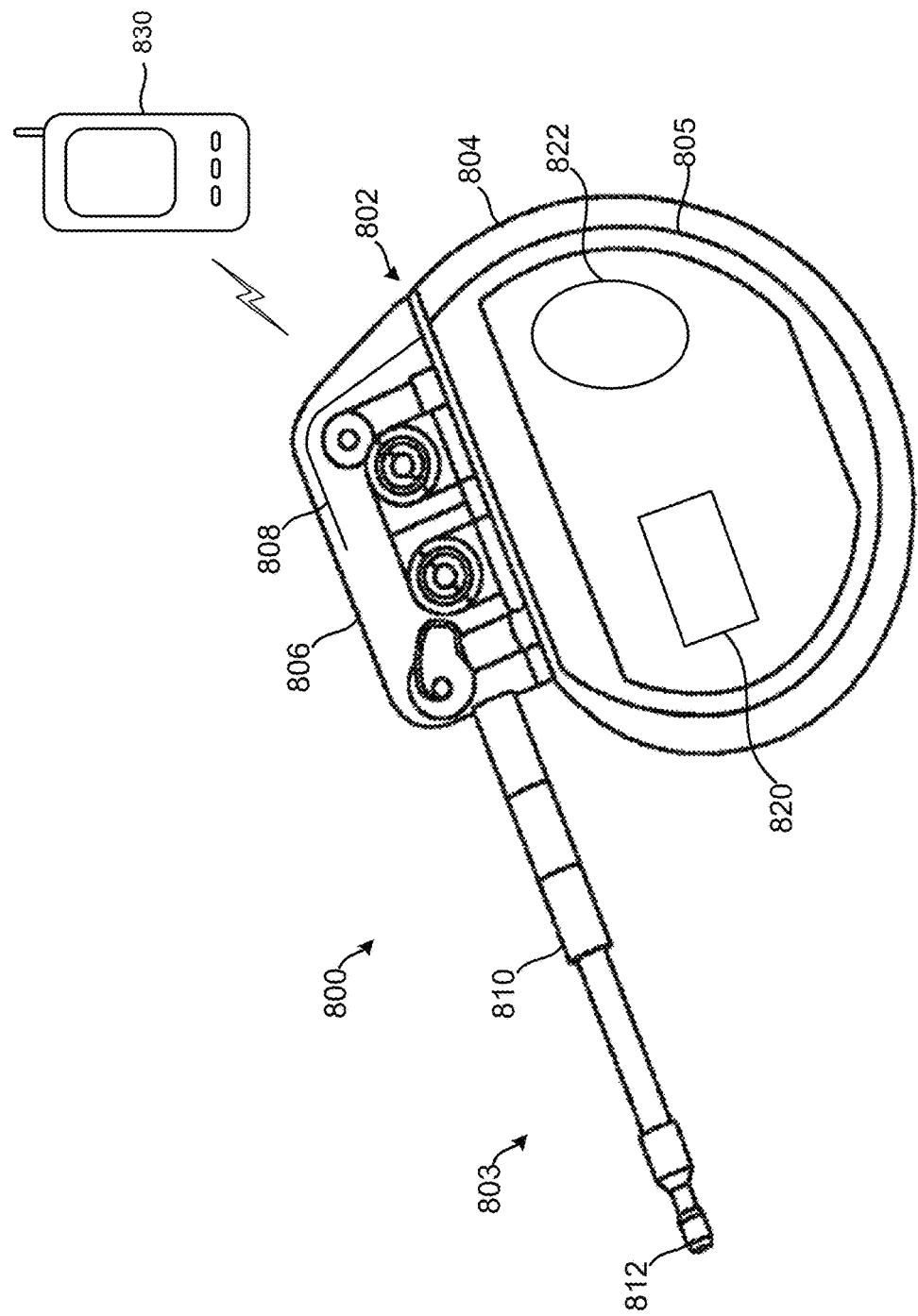
FIG. 8 is a diagram of a representative system for assessing a patient using a personalized index of patient status derived from a multiplicity of HRV measurements in accordance with various embodiments.

Embodiments of the present disclosure can be implemented in a patient monitoring device, which can be an implantable device (e.g., subcutaneous extra-thoracic device, intra-thoracic device), a cutaneous patient-external device, or a hybrid device having both patient-internal and patient-external components. For example, embodiments can be implemented in monitoring stations that remotely processes the data offline to produce diagnostic information. A patient monitoring device configured to assess patient status in accordance with embodiments of the disclosure can be incorporated in a variety of system implementations, a representative example of which is shown in FIG. 8. The system includes a patient monitoring device 800 implanted in a body of a patient, and an external component 830. When implanted, the device 800 may collect physiological data from the patient and compute HRV and HRV indices for assessing patient status in accordance with embodiments of the disclosure.

In accordance with various embodiments, a patient monitoring device may be implemented as an implantable loop recorder, which may be leadless or may include one or more subcutaneous leads. A representative embodiment of such a patient monitoring device is illustrated in FIG. 8. The patient monitoring device illustrated in FIG. 8 is configured to record an electrical physiologic signal, such as an EGG signal for the patient, from which various diagnostic information (e.g., HRV and HRV ratios) can be derived. It is understood that the devices illustrated herein are disclosed for illustrative purposes, and that methods and apparatuses of the present disclosure may be implemented in a variety of implantable and external embodiments.

FIG. 8 illustrates a representative patient monitoring device 800 that can be subcutaneously implanted under a patient's skin, typically in a pectoral region of a patient's thorax, in accordance with various embodiments. The device 800 may be a minimally invasive implantable monitoring device that senses and records a physiologic parameter, such as electrical activity of the heart, within a body of a patient. In some implementations, the device 800 is an implantable monitoring device that senses and records a physiologic parameter, such as an ECG signal, within the body of the patient and wirelessly transmits information associated with the physiologic parameter to an external device or system 830. Such a monitoring-only device that records cardiac electrical information may be implanted in a human patient for a relatively short period of time, such as a few months for example.

Other physiologic parameters or combinations of parameters, such as other electrical physiologic signals (e.g., EMG signal, bio-impedance signal), mechanical signals (e.g., blood pressure signal, blood flow signal, pulse oximetry), chemical signals (e.g., glucose), temperature and the like may similarly be recorded by the device 800 in various implementations. The description that follows will focus without limitation on implementations where the device 800 is used to monitor a subcutaneous ECG signal, but in other implementations such monitoring could be combined with or substituted by other monitoring functions.

The implantable device 800 shown in FIG. 8 includes a proximal section 802 and a distal section 803. The proximal section 802 includes a housing 804 within which various components of the device 800 are disposed, including electronic circuitry 820 (e.g., processor(s), memory) and a battery 805, which may be single-use or rechargeable in various implementations. The housing 804 may be configured to include one or more electrodes, an example of which is shown as electrode 822. All or a portion of the housing 804 may be configured as an "active can," and may further include an indifferent electrode (not shown) which is electrically isolated from the housing electrode(s) 822. A header 806 is connected to the housing 804 and to a distal extension 810, which is generally flexible or shapeable. A distal electrode 812 is disposed at a distal end of the extension 810. The header 806 serves to electrically couple the distal electrode 812 and any other electrical or optical component of the distal extension 810 with components within the housing 804 (e.g., electronic circuitry 820). An antenna 808 is shown extending from the housing 804 and into the header 808. The antenna 808 is configured for telemetering data from the implantable device 800, and can be configured to effect bi-directional wireless communication with a patient-external device or system, such as device 830. In some embodiments, the antenna 808 can be incorporated into the distal extension 810.

A handheld computing device 830 may be programmed to communicate wirelessly (e.g., transmit or receive data via radio frequency telemetry) with the implantable device 800. In some implementations, an external charging device (not shown) may be used to periodically recharge a battery 805 of the implantable device 800, though the device 800 may alternatively use a single-use battery in some implementations.

In various implementations, the patient may use the handheld device 830 to manually initiate data collection by the device 800 (e.g., initiate ECG signal sensing and recording). For example, if the patient feels lightheaded or feels palpitations in her chest, she may press a button on the handheld device 830, and the handheld device 830 may wirelessly command the device 800 to record and store physiologic data. The device 800 may also record a physiologic signal when it determines that such recording may provide useful information. For example, the device 800 may monitor a physiologic parameter (e.g., heart rate), and may record an ECG signal based on predetermined characteristics of the physiologic parameter. According to various implementations, the device 800 can be configured to record sensed physiologic information according to a predetermined schedule, in addition to recording at least ECG data for purposes of assessing patient status as described hereinabove.

The device 800 may periodically transmit collected data to the handheld device 830, such as every few hours or once per day, for example. The device 800 may also transmit collected HRV and HRV index data as described hereinabove. In some implementations, the device 800 may transmit sensed data in real time to the handheld device 830, and the handheld device 830 may store the data in internal memory or display the data as a waveform, graph, or otherwise on a display screen of the handheld device 830.

The handheld device 830 is configured to wirelessly communicate with the cloud (e.g., the Internet) via a cellular or Wi-Fi connection, and to establish a connection with a remote server. The handheld device 830 may send and receive data to/from the server. In some embodiments, the handheld device 830 may transmit data through the cloud and to the remote server, where the data may be processed and analyzed automatically (e.g., algorithmically by the server) and/or by a physician or a health care provider.

Thresholds can be computed and/or verified at the server and transmitted to handheld device 830 for upload to the device 804. In some implementations, data analysis may occur within one or both of the device 800 and the handheld device 830 (or in a distributed manner between two or more of these components). Data analysis can include detection of cardiac events/disease progression and other anomalies based on the collected data and trending of such detection and threshold data. Data analysis can also include monitoring and tracking of a disease and status of the patient 830.

Figure 9:
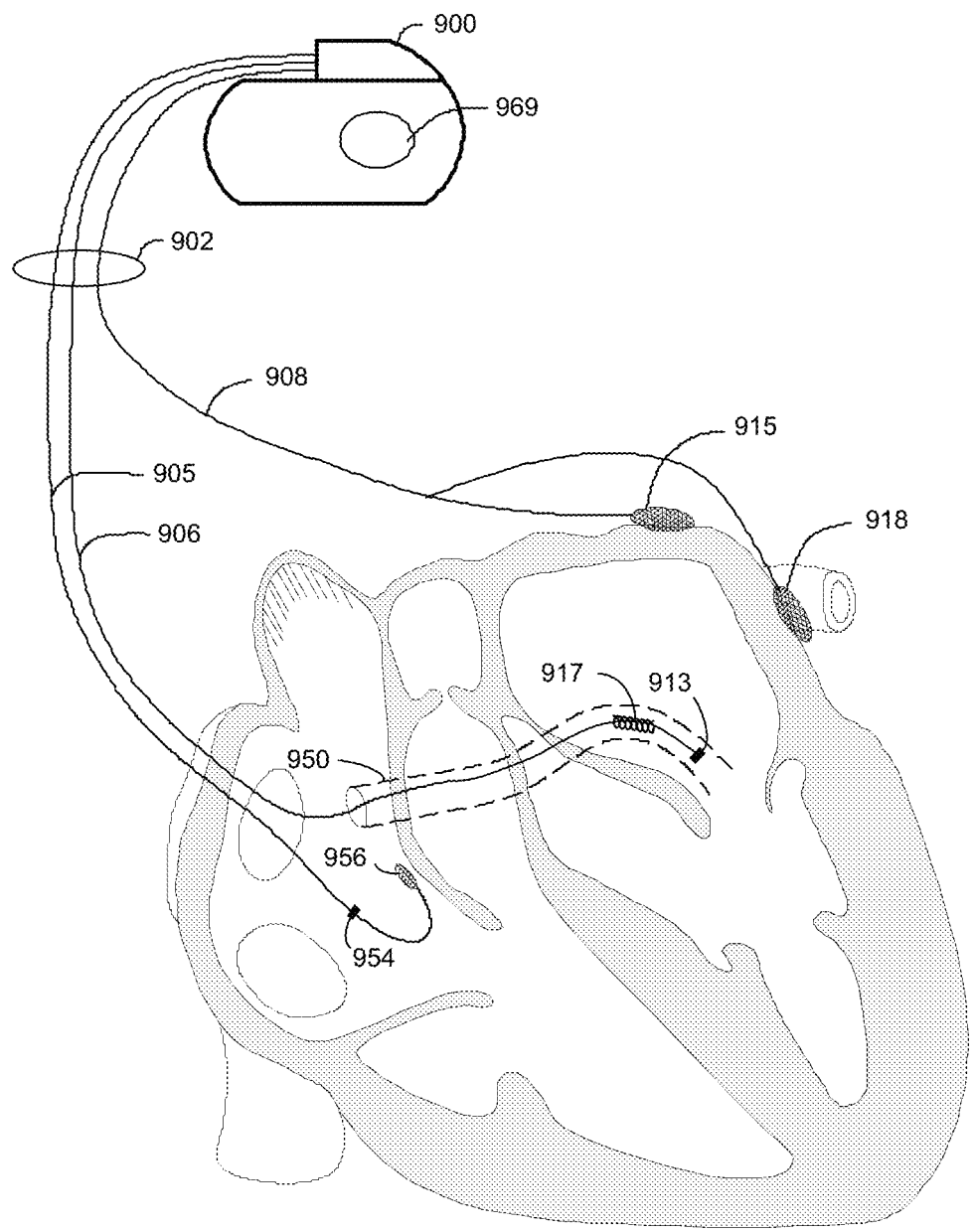
FIG. 9 is a diagram of a representative system for assessing a patient using a personalized index of patient status derived from a multiplicity of HRV measurements and for delivering electrical cardiac therapy in accordance with various embodiments.

Referring now to FIG. 9, there is illustrated an embodiment of an implantable medical device configured to deliver one or more of anti-tachycardia pacing (ATP), cardioversion, and defibrillation therapy to the right and/or left atria. The medical device includes software and/or circuitry configured to compute and monitor a personalized index of patient status derived from a multiplicity of heart rate variability measurements in accordance with various embodiments disclosed herein. The medical device is also configured to monitor for changes in patient status indicative of atrial fibrillation, and to deliver AF therapy to treat detected AF.

The medical device in FIG. 9 includes a cardiac rhythm management (CRM) device 900 electrically and physically coupled to a lead system 902. The housing and/or header of the CRM device 900 may incorporate one or more electrodes used to provide electrical stimulation energy to the heart and to sense cardiac electrical activity. The CRM device 900 may utilize all or a portion of the CRM device housing as a can electrode 969. The lead system 902 is used to detect cardiac electrical signals produced by the heart and to provide electrical energy to the heart under certain predetermined conditions to treat cardiac arrhythmias (e.g., AF). The lead system 902 may include one or more electrodes used for pacing, sensing, and/or defibrillation. In the embodiment shown in FIG. 9, the lead system 902 includes an intracardiac right atrial (RA) lead system 905 and one of an intracardiac left atrial (LA) lead system 906 and an epicardiac left atrial (LA) lead system 908. It is understood that other leads and/or electrodes may additionally or alternatively be used, and that all of the leads and/or electrodes shown in FIG. 9 need not be included in all embodiments.

The intracardiac LA lead 906 includes an LA distal electrode 913 and an LA proximal electrode 917 located at appropriate locations relative to the left atrium, such as in the coronary sinus 950. Unipolar pacing and/or sensing of the left atrium may be accomplished, for example, using the LA distal electrode 913 to the can 969 pacing vector, as can anti-tachycardia pacing therapy for the left atrium. In some implementations, an LA ring electrode (not shown) or defibrillation electrode 917 can be used together with the LA distal electrode 913 to implement bipolar pacing and/or sensing of the left atrium. LA proximal electrode 917 (e.g., coil electrode) can be used together with the can 969 to provide defibrillation therapy to the left atrium.

The epicardial LA lead 908 includes an LA distal electrode 918 and an LA proximal electrode 915 positioned at appropriate locations outside the heart for sensing and pacing the left atrium. Unipolar pacing (including ATP therapy) and/or sensing of the left atrium may be accomplished, for example, using the LA distal electrode 918 to the can 969 pacing vector. The LA proximal 915 and LA distal 918 electrodes may be used together to implement bipolar pacing and/or sensing of the left atrium, as well as ATP therapy to the left atrium.

The right atrial lead 905 includes a RA-tip electrode 956 and an RA-ring electrode 954 positioned at appropriate locations in the right atrium for sensing and pacing the right atrium. In one configuration, the RA-tip 956 referenced to the can electrode 969, for example, may be used to provide unipolar pacing and/or sensing in the right atrium. In another configuration, the RA-tip electrode 956 and the RA-ring electrode 954 may be used to implement bipolar pacing and/or sensing. The RA electrodes can be used to deliver ATP therapy to the right atrium. Although not shown in FIG. 9, the lead system 902 may also include a right ventricular lead system, which can include an RV-tip electrode, an RV-ring electrode, and an RV-defibrillation electrode (e.g., coil electrode), for example.

CONCLUSION

The above description is intended to be illustrative, and not restrictive. For example, the above-described examples (or one or more aspects thereof) may be used in combination with each other. Other examples may be used, such as by one of ordinary skill in the art upon reviewing the above description. Also, in the above Detailed Description, various features may be grouped together to streamline the disclosure. This should not be interpreted as intending that an unclaimed disclosed feature is essential. Rather, inventive subject matter may lie in less than all features of a particular disclosed example.

What is claimed is:

1. A method implemented by an implantable medical device, comprising:
    detecting a cardiac electrical signal from a patient;
    computing a first measure of heart rate variability (HRV) using the cardiac electrical signal, the first measure of HRV comprising one of a daytime measure and a nighttime measure of the patient's HRV;
    computing a second measure of HRV using the cardiac electrical signal, the second measure of HRV comprising the other of the daytime measure and the nighttime measure of the patient's HRV;
    producing an index of patient status derived from a ratio of the first and second measures of HRV, such that the index is a normalized HRV metric personalized to the patient; and
    diagnosing a change in the patient's status using the index;
    wherein each of detecting, computing, producing, and diagnosing is performed by the implantable medical device.

2. The method of claim 1, wherein each of the first and second HRV measures is a different one of:
    a baseline measure of the patient's HRV;
    a peak measure of the patient's HRV;
    a maximum measure of the patient's HRV;
    a minimum measure of the patient's HRV;
    a measure of the patient's HRV during a period of high patient activity; and
    a measure of the patient's HRV during a period of low patient activity.

3. The method of claim 1, wherein:
    the first HRV measure is an instantaneous measure of the patient's HRV at a first prescribed time or during a physiologic episode; and
    the second HRV measure is one of a measure of the patient's HRV at a second prescribed time differing from the first prescribed time, a baseline of the patient's HRV, and a measure of the patient's HRV during a physiologic episode.

4. The method of claim 3, wherein the physiologic episode comprises aberrant cardiac activity or a physiologic response to a drug administered to the patient.

5. The method of claim 1, wherein diagnosing the change in the patient's status comprises determining, by the implantable medical device, patient compliance to a medication regimen using a deviation of the index from a threshold indicative of lapse of medication effectiveness, wherein the threshold is a predetermined threshold.

6. The method of claim 1, wherein diagnosing the change in the patient's status comprises determining, by the implantable medical device, patient compliance to a medication regimen using a deviation of the index from a threshold indicative of lapse of medication effectiveness, wherein the threshold is an adaptive threshold.

7. The method of claim 1, further comprising trending, by the implantable medical device, the index and generating chronic assessment data of the patient's status.

8. The method of claim 1, wherein diagnosing the change in the patient's status comprises diagnosing further comprising detecting, by the implantable medical device, atrial fibrillation using the index, wherein the ratio of the patient's first and second HRV measures deviates from a predetermined threshold indicative of the presence of atrial fibrillation for a specified heart rate.

9. The method of claim 1, wherein diagnosing the change in the patient's status comprises diagnosing, by the implantable medical device, atrial fibrillation using the index, wherein the ratio of the patient's first and second HRV measures deviates from an adaptive threshold indicative of the presence of atrial fibrillation for a specified heart rate.

10. The method of claim 1, wherein the index defines a primary index and the method further comprises:
computing a third measure of heart rate variability (HRV) using the cardiac electrical signal;
computing a fourth measure of HRV using the cardiac electrical signal, the fourth measure of HRV differing from the third measure of HRV;
producing a secondary index of patient status derived from a ratio of the third and fourth measures of HRV reflective of a secondary patient situation, condition or time period; and
producing a tertiary index of patient status derived from a ratio of the primary and secondary indices.

11. The method of claim 1, wherein the index defines a first index and the method further comprises:
computing a third measure of heart rate variability (HRV) using the cardiac electrical signal;
computing a fourth measure of HRV using the cardiac electrical signal, the fourth measure of HRV differing from the third measure of HRV; and
producing a second index of patient status derived from a ratio of the third and fourth measures of HRV, such that the second index is a normalized HRV metric personalized to the patient;
wherein diagnosing the change in the patient's status comprises diagnosing, by the implantable medical device, atrial fibrillation using a comparison of the first and second indices, wherein agreement of the first and second indices serves as a confirmatory result and a lack of agreement of the first and second indices serves as an indicator prompting additional analysis for atrial fibrillation detection.

12. A medical device, comprising:
a housing configured for implantation within a body of a patient;
detection circuitry disposed in the housing and coupled to an electrode arrangement, the detection circuitry configured to sense a cardiac electrical signal from the patient; and
a processor disposed in the housing and coupled to the detection circuitry, the processor configured to:
compute a first measure of heart rate variability (HRV) using the cardiac electrical signal, the first measure of HRV comprising one of a daytime measure and a nighttime measure of the patient's HRV;
compute a second measure of HRV using the cardiac electrical signal, the second measure comprising the other of the daytime measure and nighttime measure of the patient's HRV;
produce an index of patient status derived from a ratio of the first and second measures of HRV, such that the index is a normalized HRV metric personalized to the patient; and
diagnose a change in the patient's status using the index.

13. The device of claim 12, wherein each of the first and second HRV measures is a different one of:
a baseline measure of the patient's HRV;
a peak measure of the patient's HRV;
a maximum measure of the patient's HRV;
a minimum measure of the patient's HRV
a measure of the patient's HRV during a period of high patient activity; and
a measure of the patient's HRV during a period of low patient activity.

14. The device of claim 12, wherein the processor is configured to diagnose patient compliance to a medication regimen using a deviation of the index from a threshold indicative of lapse of medication effectiveness, wherein the threshold is a predetermined threshold.

15. The device of claim 12, wherein the processor is configured to diagnose patient compliance to a medication regimen using a deviation of the index from a threshold indicative of lapse of medication effectiveness, wherein the threshold is an adaptive threshold.

16. The device of claim 12, wherein the processor is further configured to trend the index and generate chronic assessment data of the patient's status.

17. The device of claim 12, wherein the processor is configured to diagnose atrial fibrillation using the index, wherein the ratio of the patient's first and second HRV measures deviates from a predetermined threshold indicative of the presence of atrial fibrillation for a specified heart rate.

18. The device of claim 12, wherein the processor is configured to diagnose atrial fibrillation using the index, wherein the ratio of the patient's first and second HRV measures deviates from an adaptive threshold indicative of the presence of atrial fibrillation for a specified heart rate.

19. The device of claim 12, wherein the index defines a primary index and the processor is further configured to:
compute a third measure of heart rate variability (HRV) using the cardiac electrical signal;
compute a fourth measure of HRV using the cardiac electrical signal, the fourth measure of HRV differing from the third measure of HRV;
produce a secondary index of patient status derived from a ratio of the third and fourth measures of HRV reflective of a secondary patient situation, condition or time period; and
produce a tertiary index of patient status derived from a ratio of the primary and secondary indices.

20. The device of claim 12, wherein the index defines a first index and the processor is further configured to:
- compute a third measure of heart rate variability (HRV) using the cardiac electrical signal;
- compute a fourth measure of HRV using the cardiac electrical signal, the fourth measure of HRV differing from the third measure of HRV;
- produce a second index of patient status derived from a ratio of the third and fourth measures of HRV, such that the second index is a normalized HRV metric personalized to the patient; and
- diagnose atrial fibrillation using a comparison of the first and second indices, wherein agreement of the first and second indices serves as a confirmatory result and a lack of agreement of the first and second indices serves as an indicator prompting additional analysis for atrial fibrillation detection.

* * * * *

UNITED STATES PATENT AND TRADEMARK OFFICE
CERTIFICATE OF CORRECTION

Page 1 of 1

PATENT NO. : 9,901,266 B2
APPLICATION NO. : 14/738022
DATED : February 27, 2018
INVENTOR(S) : Rodolphe Katra It is certified that error appears in the above-identified patent and that said Letters Patent is hereby corrected as shown below:

In the Claims

Column 17, Lines 21-22 (Claim 8, Lines 2-3) after the word "diagnosing" delete the words "further comprising detecting"

Signed and Sealed this
Tenth Day of September, 2019

Andrei Iancu
*Director of the United States Patent and Trademark Office*